United States Patent [19]
Haskell

[11] Patent Number: 5,550,383
[45] Date of Patent: Aug. 27, 1996

[54] REMOLDABLE THERMOPLASTIC RADIATION SHIELD FOR USE DURING RADIATION THERAPY

[76] Inventor: Douglas A. Haskell, 449 Amhurst Rd., Valparaiso, Ind. 46383

[21] Appl. No.: 423,231

[22] Filed: Apr. 17, 1995

[51] Int. Cl.$^6$ .................................................. G21F 3/02
[52] U.S. Cl. ................................... 250/519.1; 250/515.1
[58] Field of Search ........................ 250/515.1, 519.1; 378/185, 186

[56] References Cited

U.S. PATENT DOCUMENTS

| | | | |
|---|---|---|---|
| 3,818,234 | 6/1974 | Atkins et al. | 250/515.1 |
| 4,699,743 | 10/1987 | Nakamura et al. | 264/104 |
| 4,957,943 | 9/1990 | McAllister et al. | 521/64 |
| 4,963,291 | 10/1990 | Bercaw | 252/512 |
| 5,130,342 | 7/1992 | McAllister et al. | 521/61 |
| 5,190,990 | 3/1993 | Eichmiller | 523/137 |
| 5,278,219 | 1/1994 | Lilley et al. | 524/439 |

OTHER PUBLICATIONS

Farahani and Eichmiller, "Metal–Polysiloxane Shields for Radiation Therapy of Maxillo–Facial Tumors," Medical Physics, vol. 18, No. 2 (Mar./Apr. 1991), pp. 273–278.

*Primary Examiner*—Bruce C. Anderson
*Attorney, Agent, or Firm*—Gary M. Hartman; Domenica N. S. Hartman

[57] ABSTRACT

A shielding device is provided for protecting healthy tissue during radiotherapy of malignant tissue. The shielding device is composed of nontoxic, high atomic weight metal particles that are dispersed in a thermoplastic matrix material that is substantially rigid at temperatures encountered during radiotherapy, yet becomes readily moldable at temperatures that are within a comfortable range for a patient so as to enable in situ molding of the device. Because the matrix material is a nonsetting thermoplastic, the shielding device can be continuously reshaped in order to achieve a better fit for a patient and the radiation beam used. In addition, the shielding device can be readily reshaped in order to ensure an adequate thickness for radiation shielding.

20 Claims, 2 Drawing Sheets

REMOLDABLE THERMOPLASTIC RADIATION SHIELD FOR USE DURING RADIATION THERAPY

BACKGROUND OF THE INVENTION

1. Field of the Invention

The present invention generally relates to devices used in radiation therapy for the purpose of shielding from radiation exposure those areas unintended for treatment. More particularly, this invention relates to a radiation shield composed of a radiation-absorbing material dispersed within a thermoplastic matrix material that enables the shield to be readily molded and subsequently remolded for reuse a potentially infinite number of times, so as to yield a radiation shield that is highly effective and practical for use in radiation therapy.

2. Description of the Prior Art

In the treatment of malignancies using electron, gamma and x-ray radiation, modalities of therapy will vary according to tumor cell type, stage of lesion, degree of anaplasia, radioresistance of the malignancy and, finally, what healthy tissues will be altered or destroyed during the tumor irradiation process. Malignant tumors in the mouth, and head and neck regions generally require a mean therapeutic dosage of about 5000 to about 7000 centigray (cGy) in increments of 180 cGy per day, on a schedule of about five treatments per week. In some instances, about 4000 to about 5000 cGy may be initiated to the lymph nodes of the neck. In all cases, it is of concern to minimize damage to healthy tissue surrounding the cancerous tissue intended to be destroyed by therapy, in that cellular damage from radiation therapy, or radiotherapy, can range from minor cutaneous erythema to life-threatening osteoradenonecrosis.

To minimize injury to healthy tissue, radiation shields have been used for radiotherapy of highly localized regions of the body, including the thyroid, esophagus, laryngeal, tonsilar, sinus, basal and squamous, as well as for radiotherapy of melanoma near anatomic structures containing radio sensitive cells, such as the lip, eye, lacrimal ducts, ear, scalp and nasal mucosa. Additional uses of radiation shields include intra oral prosthesis for protecting the salivary glands, mucosa, tongue and dentosseous areas from injury such as xerostomia (dry mouth), loss of taste, mucositis, post radiation infection, radiation caries and osteoradenonecrosis. In particular, examples of oral tissue complications due to radiotherapy include mucositis from dosages in excess of greater than about 1000 cGy, erythatous mucositis from dosages in excess of about 2500 cGy, loss of taste from dosages in excess of about 3000 cGy, up to about 57% loss of salivary function from dosages in excess of about 1000 cGy, irreversible xerostomia from dosages in excess of about 4000 cGy, and mean beginning of osteoradenonecrosis from dosages in excess of about 5900 cGy.

Prior art shielding devices have generally entailed shields or stents formed as customized rigid prosthetic devices or from a moldable lead-filled clay. An example of an intra orally shield employed in the art utilizes Lipowitz metal containing toxic lead and cadmium, and entails a very time consuming impression, cast and fabrication process. While shielding devices formed from lead-filled clay have found use because they are remoldable, their use is limited by significant disadvantages and shortcomings. For example, lead-filled clay shields never exist in a rigid plastic state, and have relatively poor flow characteristics such that they do not readily capture fine anatomic detail in tumor fields. A consequence of their continual moldable character is that these devices have a tendency to change shape whenever handled, such as during removal from a patient, and must often be reshaped or remolded for each therapy session. Furthermore, it is difficult to measure the degree of radioresistance of these devices for use in critical radiosensitive healthy cellular organelles because they bend and distort when an attempt is made to gauge their thickness with a caliper.

In addition to the above, the lead particles of lead-filled clay shields tend to leach out of the clay and form a black oil residue that will leave marks on the patient's tissue. Such a tendency exacerbates the well known toxic nature of lead, rendering such devices particularly incompatible for intra oral use and at extra oral post-surgical wound sites, even for minimal exposures. Furthermore, lead-filled clay shielding devices are generally unable to absorb electron backscatter, which occurs with gamma and x-ray sources and pertains to the low energy electrons and positrons that are reflected and scattered by radiation shield materials. Finally, because lead-filled clay shields tend to become readily distorted, they cannot be used to precisely retarget the radiation field relative to the exact tumor location and with respect to healthy tissues before each radiation treatment.

An alternative to lead-filled clays is taught in U.S. Pat. No. 5,190,990 to Eichmiller, wherein particles of a nontoxic metal are dispersed in a moldable elastomeric base-catalyst thermosetting material. More specifically, Eichmiller teaches the use of various metal alloy spheroid particles in an addition-reaction polymerizable elastomeric precursor or resin, such as vinyl polysiloxane resin or silicone resin. The nontoxic metals suggested by Eichmiller offer greater safety to the patient than does a lead-filled clay, particularly for intra oral use. However, a significant drawback of the shield taught by Eichmiller is that the shield material is a thermoset, and therefore not remoldable, such that the shield's anatomic shape is irreversible. Such a limitation necessitates that the shield be trimmed with a knife or supplemented with additional polymer in order to ultimately achieve a suitable fit for radiotherapy, as well as provide the necessary thickness in order to ensure that adequate radioresistance is provided for the surrounding healthy tissue. Furthermore, Eichmiller's shield must generally be discarded after radiotherapy is completed for a particular patient, since it is highly unlikely that the shield will appropriately fit any other patient.

Because the thermosetting materials taught by Eichmiller are addition-reaction compositions, another complication is that a limited period of time is available during which the shield is moldable before the material permanently sets. Consequently, shields fabricated in accordance with Eichmiller are practically limited to being mixed and compounded in the clinic where treatment is to occur. In order to achieve a uniform distribution of metal particles within the thermosetting material, and therefore provide uniform radioresistance throughout the shield, the metal particles must be admixed while the thermosetting material is still highly workable. This constraint, and because the precured thermosetting materials may have a gel-like consistency, impedes the ability to achieve a uniform distribution of metal particles in the compound. As a result, the radioresistance of the shield may be reduced in localized regions, leading to exposure of healthy tissue to harmful levels of radiation. Another complication is that the time span for mixing the particles may be further limited if excess curing agent is used, or if the temperature of the compound or room is higher than that recommended for mixing. Consequently, the shield fabricator may not have adequate time to mix the compound and then make an accurate impression prior to the thermosetting material taking a permanent set.

Thus, it would be desirable to provide a radiation shielding device whose composition provides the necessary protection to healthy tissue during radiotherapy, is able to block backscatter electrons, and avoids the toxicity and permanent deformable nature of clay-based devices, yet is capable of being readily formed and remolded in order to enable the shield to be better tailored to the physical features of a particular patient, remoldable to adapt to changes in patient physiology and radiotherapy. Advantageously, such a shield could be readily reused with other patients if sterilized, heated and then remolded.

SUMMARY OF THE INVENTION

It is an object of this invention to provide a radiation shielding device for use during radiotherapy of malignant tissue.

It is a further object of this invention that such a device be composed of nontoxic materials, such that the device can be employed intra orally.

It is another object of this invention that such a device be substantially rigid at body temperatures to resist deformation while in use during repeated radiotherapy on a patient.

It is yet another object of this invention that such a device be readily moldable at temperatures that enable the device to be comfortably molded in situ on the patient.

It is yet a further object of this invention that such a device be capable of forming an electron backscatter shield at the shield-tissue interface.

Lastly, it is an object of this invention that such a device be readily remoldable so as to enable the device to be reshaped and reconfigured, adaptable to changing tumor conditions, and allow its use for subsequent treatments with other patients.

In accordance with a preferred embodiment of this invention, these and other objects and advantages are accomplished as follows.

According to the present invention, there is provided a shielding device for protecting healthy tissue during radiotherapy of malignant tissue. The shielding device is composed of nontoxic, high atomic weight metal particles that are dispersed in a thermoplastic matrix material that is substantially rigid at temperatures encountered during use, yet becomes readily moldable at temperatures that are within a comfortable range for a patient so as to enable in situ molding of the device. Because the matrix material is a nonsetting thermoplastic, the shielding device can be continuously reshaped in order to achieve a better fit for a patient. In addition, the shielding device can be readily reshaped and supplemented with additional material in order to provide an adequate thickness that will ensure proper radiation shielding.

In accordance with this invention, the thermoplastic matrix material yields a moldable impression compound that is capable of capturing considerable anatomic detail. The matrix material is preferably a hydrocarbon wax blend that is characterized by being a solid at about 35° C. but readily moldable at temperatures of about 45° C. and greater. As such, the preferred matrix material is resistant to flow at typical body temperatures (about 38° C.), yet is highly moldable at temperatures that can be comfortably tolerated (about 40° C. to about 50° C.) by a patient, so as to permit in situ molding of the shielding device.

An additional advantage of the preferred thermoplastic matrix material is that it has a specific gravity of about 1.66. As a result, the material in its untitled form is capable of stopping electron backscatter during radiotherapy. Accordingly, untitled thermoplastic material can be added when an electron backscatter block is desired between the shielding device and any adjacent healthy tissue that would otherwise be subjected to backscatter and its ulcerative sequela.

A preferred nontoxic high atomic weight metal for the shielding device of this invention is bismuth metal particles. Bismuth has found usage as a radiation shielding element for nuclear reactors because of its high atomic weight (208.98) and the vast temperature difference between its melting point (271° C.) and its boiling point (1560° C.). In accordance with this invention, bismuth is preferred as a shielding material for radiotherapy due to it being biocompatible, nontoxic and nonradioactive, having low thermal conductivity and, most important, having a high atomic mass for greater radioresistance. Advantageously, bismuth and bismuth compounds have been determined to have little or no effect on intact skin or mucous membranes, with a lethal dose (LD) low of about 221 mg/kg of body weight. Furthermore, usage of bismuth and its alloys in various pharmocologic preparations for gastrointestinal pacification is well documented. As such, the enhanced ingestion quality of bismuth would allow for construction of intra oral radiation splints where trace amounts of compound-bound bismuth could be ingested without medical ramifications.

In addition to the above, it has been found that a high elemental bismuth ratio can be achieved in the preferred thermoplastic compound of this invention, enabling the shielding device to maintain its precise-shaped anatomic form. Because bismuth has very low thermal conductivity as compared to other metals, the shielding material of this invention cools slowly so as to provide ample time during which the material can be molded after heating.

Oncologic treatment with the shielding device of this invention involves manually molding the device while in a plastic flow state. For oral radiotherapy, an extra or intra oral splint can be fabricated from the thermoplastic material to protect surrounding healthy tissues from the sequela of radiotherapy. A customized, anatomically and therapeutically correct radiation shield can be readily molded with the metal-filled thermoplastic matrix material by elevating the temperature of the material to about 45° C. or more, and then positioning the material in the region to be irradiated. Due to its minimal flow characteristics at temperatures below about 40° C., the material returns to its original solid state while in position on the patient, after which the now-molded shielding device can be removed and measured to ensure its thickness is suitable for providing the required radiation protection.

In view of the above, it can be seen that prior art shielding devices, and particularly lead-filled clay shields, are inferior to the thermoplastic remoldable shielding device of the present invention. For example, significant advantages of employing the shielding device of the present invention include the use of stable materials that are nontoxic, noncarcinogenic and nonhazardous, enabling the use of the shielding device for both intra and extra oral impression and molding. The preferred bismuth particles and thermoplastic material are stable and compatible with each other, enabling high homogeneous loading of the high atomic mass metal to maximize the radiation shielding effect.

Another significant advantage is the ability of the preferred thermoplastic material to readily capture fine anatomic detail, and subsequently attain a rigid state after molding that permanently preserves the desired detail. In particular, the thermoplastic material is characterized by being a solid at temperatures of about 35° C. and below, yet readily moldable at temperatures that are well within tolerance levels for human tissue to accurately capture the anatomy to be protected. The solid shield can also be easily trimmed with a rotary bur or lathe if necessary to make slight alterations or to form portals through the shielding device through which irradiation occurs.

Furthermore, the matrix material of the shielding device is a thermoplastic material that undergoes a reversible change of state, such that repeated adjustments can be made in clinical situations for a more precise shield. Such a capability is in contrast to prior art thermosetting compounds that undergo an irreversible base-catalyst polymerization reaction, and therefore cannot be subsequently remolded. Should a greater thickness be required or a change occur in the anatomic contour or the shape field to be irradiated, the shielding device of this invention can be readily reheated and reshaped to the desired configuration in situ or by hand. Advantageously, the matrix material of this invention cools sufficiently slowly to provide an ample working time for molding and remolding.

The remoldable character of the matrix material is a further advantage in view of the material's ability to stop electron backscatter during radiotherapy. When heated appropriately, unfilled thermoplastic material can be readily added and bonded to the shielding device of this invention if an electron backscatter block is desired between the device and any adjacent healthy tissue that would otherwise be subjected to backscatter.

Other objects and advantages of this invention will be better appreciated from the following detailed description.

BRIEF DESCRIPTION OF THE DRAWINGS

The above and other advantages of this invention will become more apparent from the following description taken in conjunction with the accompanying drawings, in which.

DETAILED DESCRIPTION OF THE PREFERRED EMBODIMENT

The present invention provides an improved radiation shield that is particularly well suited for use during radiotherapy of malignancies, and particularly for the protection of healthy tissue surrounding localized malignancies, including those located in such regions as the thyroid, esophagus, laryngeal, tonsilar, sinus, basal and squamous, melanoma near anatomic structures containing radiosensitive cells, and intra oral uses for protecting the salivary glands, mucosa, tongue and dentosseous areas. The oncologic treatment made possible by this invention involves directly manually molding a metal-filled thermoplastic compound of specific manufactured radioresistance while in a plastic flow state, which becomes a solid after cooling to human body temperatures.

Figure 1:
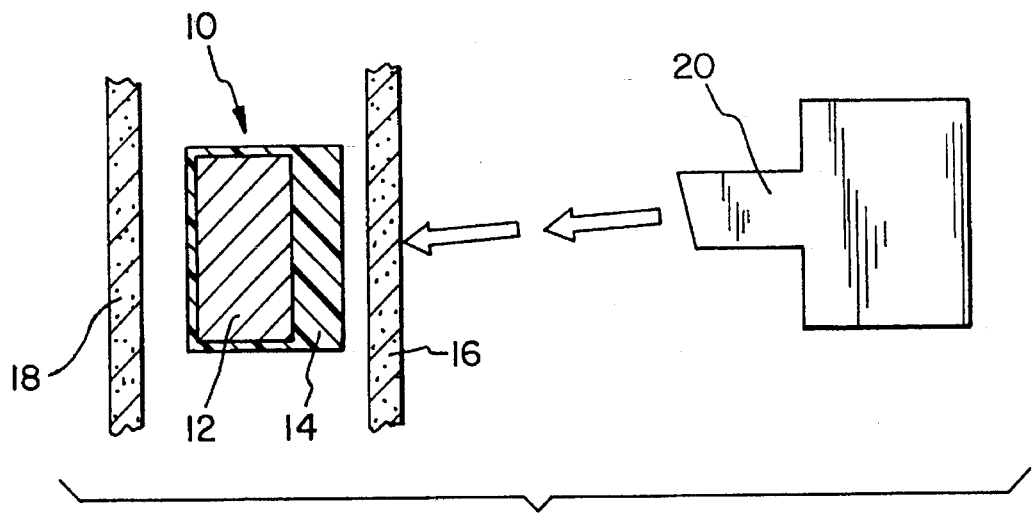
FIG. 1 schematically represents in cross-section the use of a shielding device in accordance with this invention.
Figure 2:
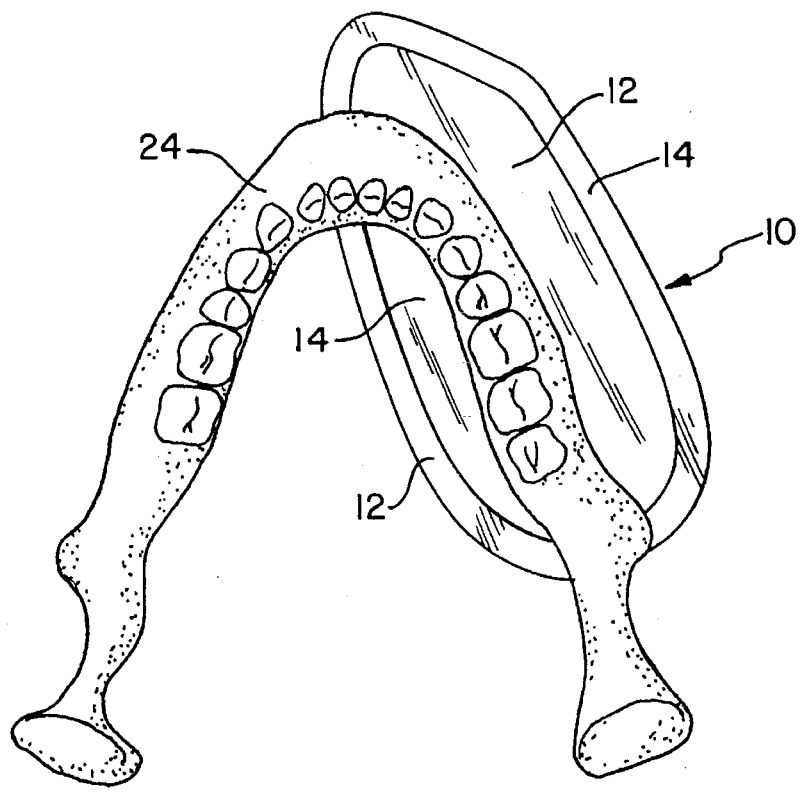
FIG. 2 represents placement of the shielding device of this invention for use in intra oral radiotherapy.
Figure 3:
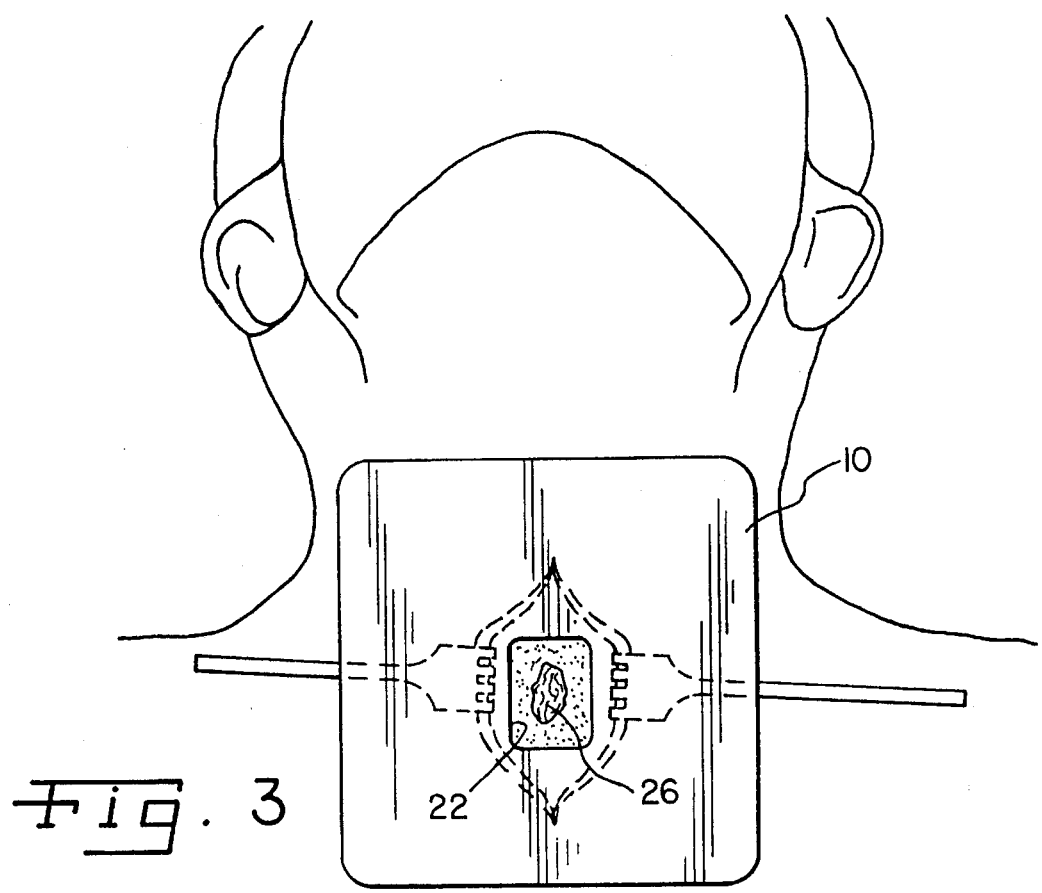
FIG. 3 represents placement of the shielding device of this invention for use in treating a malignant esophageal tumor.
Figure 4:
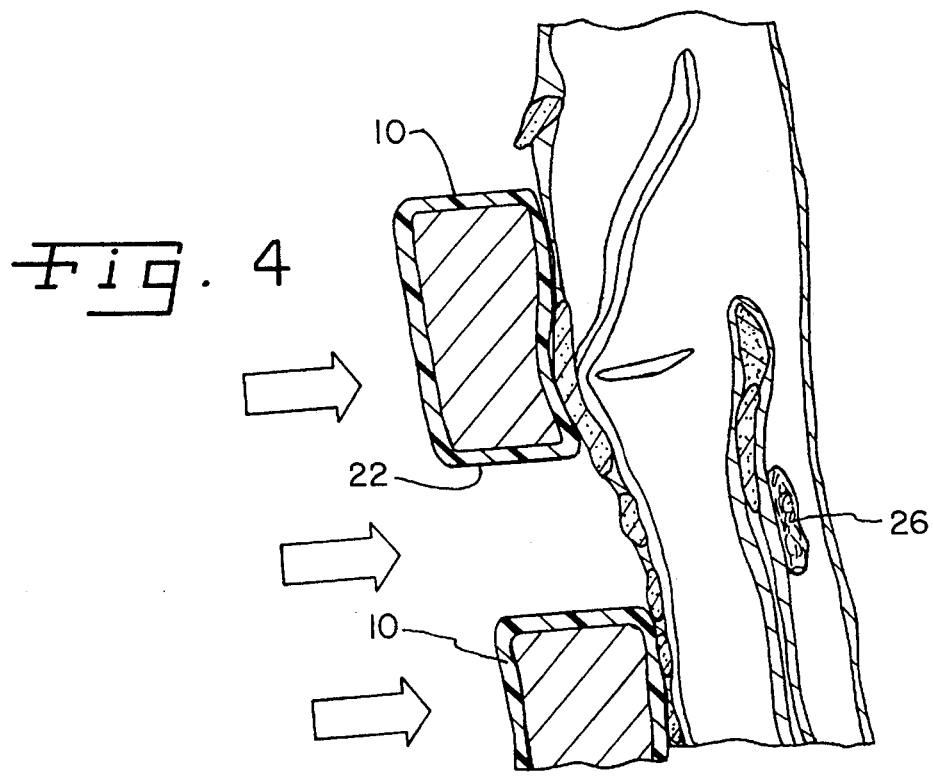
FIG. 4 is a cross-sectional representation of FIG. 3.

A radiation shield 10 in accordance with this invention is schematically illustrated in FIG. 1, while applications for the shield 10 are illustrated in more detail in FIGS. 2 through 4. Schematically illustrated in FIG. 1 is a radiation emitting device 20, such as a cobalt 60 gamma radiation source or electron radiation source of a type known in the art. The shield 10 is shown as being positioned at a region of the human anatomy where malignant tissue (not shown) is to be irradiated and where healthy tissue 18 adjacent the malignant tissue is to be protected from radiation. The shield 10 is shown as including a shielding layer 12 and a backscatter layer 14 for the purpose of protecting healthy tissue 16 between the shield 10 and the radiation emitting device 20 from electron backscatter.

In accordance with this invention, the shielding layer 12 is composed of a metal-filled thermoplastic material, while the backscatter shield 14 is formed from an unfilled thermoplastic material. The thermoplastic materials employed for the shielding and backscatter layers 12 and 14 are preferably the same, being characterized by a resistance to flow at typical body temperatures, yet highly moldable at temperatures that can be comfortably tolerated (about 40° C. to about 50° C.) by a patient so as to permit in situ molding of the shield 10. In accordance with this invention, the thermoplastic material is preferably a hydrocarbon wax blend, such as a blend referred to as an "Impression Compound" available from Moyco Industries, Inc. of Philadelphia, Pa. Other suitable hydrocarbon wax blends are commercially available from Kerr Dental of Romulus, Mich., Jelenko of Armonk, N.Y., and Mizzy of Cherry Hill, N.J. A preferred hydrocarbon wax blend is composed of about 30 parts rosin, about 30 parts copal resin, about 10 parts carnauba wax, about 5 parts stearic acid, and about 75 parts talc. The preferred hydrocarbon wax blend is further characterized by being a solid at about 35° C., flow at about 37° C. of less than about 6 percent, and flow at about 45° C. of greater than about 85 percent. It is foreseeable that a hydrocarbon wax blend containing different constituents and/or different amounts of constituents could be employed. Furthermore, it is foreseeable that a synthetic thermoplastic could be substituted for the preferred hydrocarbon wax blend if characterized by appropriate thermal properties, so as to make the thermoplastic compatible with the objects of this invention.

In addition to the above, the preferred thermoplastic material has a specific gravity of about 1.66 (i.e., a density of about 1.66 g/cm$^3$), such that the unfilled thermoplastic material is suitable for stopping electron/proton backscatter during radiotherapy. As such, unfilled thermoplastic material can be added when an electron backscatter layer 14 is desired adjacent to surrounding soft tissues.

A preferred metal for the shield 10 of the invention is a nontoxic, high atomic weight metal such as bismuth. As a shielding material for radiotherapy, bismuth is preferred due to it being biocompatible, nontoxic and nonradioactive, having low thermal conductivity and, most important, having a high atomic mass (208.98) for greater radioresistance. Advantageously, bismuth and bismuth compounds have been determined to have little or no effect on intact skin or mucous membranes. Furthermore, usage of bismuth and its alloys in various pharmocologic preparations for gastrointestinal pacification is well documented. As such, intra oral radiation splints can be formed with a bismuth-filled thermoplastic material of this invention, whereby trace amounts of compound-bound bismuth can be ingested without medical ramifications.

While bismuth is the preferred fill metal, other metals that meet the requirements for being nontoxic, biocompatible and nonradioactive and having a high atomic mass could be employed in lieu of bismuth for the shield 10. Examples of such metals include silver (Ag), Copper (Cu), tin (Sn), and palladium (Pd). Lead may also be employed as a fill metal for extra oral and non post-surgical sites. Advantageously, the thermoplastic nature of the preferred matrix material promotes encapsulation of the lead particles, thereby significantly reducing the potential for adverse toxic effects. Nonetheless, bismuth is preferred due to having certain properties that make it particularly desirable for use in the shielding layer 12 of this invention. For example, bismuth has the lowest thermal conductivity of all the solid metals. As a result, the shield 10 is more readily able to be shaped and afterwards maintain a precise-shaped anatomic form because the low thermal conductivity of bismuth minimizes the rate at which the center of the shielding layer 12 is warmed and cooled by external sources. Another advantage is that bismuth is capable of a high elemental ratio in the preferred thermoplastic materials, which promotes the radioresistive capability of a shield employing bismuth as the metal fill material. Finally, because bismuth has relatively low thermal conductivity, the tendency is reduced for the center of the shielding layer 12 to be heated to a point where it begins to flow when applying heated and untilled thermoplastic material to the shielding layer 12 for the purpose of forming the backscatter layer 14.

The shielding layer 12 of this invention can be readily produced with conventional equipment. The thermoplastic material is preferably ground to a fine powder consistency. The metal particles, preferably having a particle size of about −325 mesh (about 44 micrometers) but not greater than about −100 mesh (about 149 micrometers), is added to the powdered compound in metal:thermoplastic ratios, by volume, of about 50:50 to about 65:35. Because the mixture is dry, it can be blended for any desired length of time in order to achieve a homogeneous mixture. The mixture is then heated to a temperature sufficient to melt the thermoplastic material. For the preferred hydrocarbon wax blend, a suitable temperature is about 90° C. The molten material is again agitated to ensure dispersion of the metal particles, and then allowed to cool until hardened. The molten material may be poured into a suitable prefabricated mold so as to form a shield precursor having a desired size, thickness or configuration, such as the inclusion of a portal in the shield 10 through which radiation energy can be directed. Alternatively, a properly sized and shaped shield 10 can be molded for use in treatment scenarios where predefined shapes can be used.

For shield fabrication, an oncologic team using the shield 10 of this invention can choose, according to tumor treatment modality, a prefabricated shield, with or without a portal, or a shield precursor of suitable mass and preferably having a convenient length, width and thickness. A customized, anatomically and therapeutically correct radiation shield 10 can then be readily molded by elevating the temperature of the material to about 45° C. or more and positioning the material in the region to be irradiated, where the material is worked to conform to the anatomic detail of the region. Due to its minimal flow characteristics at temperatures below about 40° C., the material is able to return to its original solid state while in position on the patient, after which the now-molded shield 10 can be removed to ensure its thickness is suitable for providing the required radiation protection.

In practice, the above has been suitably performed by heating the shield 10 in a water bath to a temperature of about 45° C. to about 50° C. for as little as about four to five minutes. The tissue to be irradiated is marked and a petroleum jelly or other suitable substance is applied lightly to the tissue. The now plastically-malleable shield material, which is at a temperature that can be readily tolerated by the patient, is applied to the radiation and scatter field and hand molded to the desired configuration so as to protect the adjacent healthy tissue, leaving the malignant neoplasm open to the radiation beam to be employed. The radiation shield 10 is removed from the patient upon becoming sufficiently firm. Untilled thermoplastic material may be added at this time if an electron backscatter layer 14 is desired adjacent soft tissues The molded radiation shield 10 preferably remains in or on the patient for a period sufficient to allow the shield 10 to returning to its original solid state, typically requiting about seven to ten minutes, depending on the mass of the material.

Unlike elastomeric irreversible base-catalyst materials of the prior art, the reversible thermoplastic material utilized by the present invention enables the shield 10 to be reshaped and molded if necessary to achieve a more suitable fit to the radiation site. In practice, it has been found that heating the shield 10 to about 42° C. or greater will restore sufficient formability to the shield 10 in order to modify its shape. If present, a radiation portal may be enlarged or constricted at this time also. Additional layers of metal-filled thermoplastic material may also be readily added to increase the thickness of the shield 10 by warming the additional material to a temperature of about 45° C. to about 50° C. while warming the shield 10 until a slight shine is acquired on the surface, and then compressing the additional material to the shield 10.

Following fabrication, the thickness of the shield 10 is preferably confirmed to ensure that adequate radioresistance is provided by the shield 10. The tumor irradiating beam trajectory and the area of treatment field can be repeatedly correctly positioned because of the rigid exactness of the shield 10 and the anatomic detail and precise molding made possible with the preferred thermoplastic material. During the course of treatment, which typically consists of twenty to thirty radiation treatments for many malignancies, the shield 10 can be modified if necessary to promote comfort for the patient, increase the thickness of the shield 10, or resize any portal required for treatment.

The preferred bismuth-filled thermoplastic shield 10 of this invention is particularly well suited for intra oral direct molding fabrication due to the low toxicity of bismuth. Such an application is illustrated in FIG. 2, in which two shields 10 fabricated in accordance with this invention are shown as being positioned around the lower jaw 24 of a patient for radiation therapy. When molding the shields 10 for this type of treatment, particular attention and consideration should be given those tissues and organs, i.e., salivary glands and ducts, tongue, soft palate and mucosa, whose cellular structure is very radiosensitive. Intra orally, the radioresistance (i.e., thickness) of each shield 10 may vary according to the malignancy position in relation to different magnitudes of healthy tissue destruction at the same level of therapy. Extension of one of the shields 10 into the retromylohyoid mucobuccal folds and over the retromolar pad, geniohyoid and soft palate would be of benefit.

Those tissues adjacent to the shield 10 will generally be subjected to electron and neutron back scatter during treatment. These "slow" electrons, which are produced when the irradiating beam is attenuated on healthy tissues, can be negated (captured) in any material with a density of about 1.0 g/cm$^3$ and having a thickness of at least about three to five millimeters. If not negated, backscatter electrons produce localized ulcers and mucositis at the splint-tissue interface. As noted above, the preferred hydrocarbon wax blend for the shield 10 has a density of about 1.66 grams/cm$^3$, and therefore meets this basic requirement. In accordance with this invention, a suitable backscatter shield 14 can be formed with the preferred hydrocarbon wax blend by warming a mass of the untilled blend to about 49° C., and then compressing and molding the mass against the shield 10 so as to bond the untilled blend to the shield 10 and achieve a thickness of about three millimeters or more for the backscatter shield 14. Preferably, the thickness of the backscatter shield 14 is verified with a caliper and Boley gauge after solidifying.

A further example of the use of a shield 10 formed in accordance with the present invention is shown in FIGS. 3 and 4. FIG. 3 is a frontal view and FIG. 4 is a cross-sectional side view showing a malignant esophageal tumor 26 and a shield 10 configured with a portal 22 for the purpose of permitting irradiation of the tumor 26 while shielding the surrounding healthy tissue. It is apparent that the size of the portal 22 can be readily varied to correspond to the necessary radiation field for a tumor. The size of the shield 10 is generally configured in view of the beam field used, which is conventionally about ten centimeters in diameter. From FIG. 4 it is apparent that a backscatter layer 14 is not employed in the treatment of malignant tissue under the particular circumstances illustrated.

To evaluate the effectiveness of shields 10 formed in accordance with this invention, nuclear properties testing was performed on samples of the preferred bismuth-filled hydrocarbon wax blend. The apparent density of the material was about 4.5 g/cm$^3$, representing a ratio by volume of about 60 percent bismuth and about 40 percent of the thermoplastic material. The bismuth particle size was about −325 mesh (about 44 micrometers), with a rhombohedral particle shape. The small size of the bismuth particles enabled the incorporation of a large volume of bismuth into the thermoplastic material while maintaining a homogeneous consistency. Notably, it is expected that bismuth particles of greater than about −100 mesh (about 149 micrometers) would be relatively more difficult to load, increase brittleness of the shield, and decrease its molding properties.

Testing with both electron and x-rays were conducted with a Pro-Varion Clinac 2100 C-D Linear Accelerator with a ten by ten centimeter cone field. The source-to-surface distance was about one hundred centimeters. For electron and x-ray diagnostics, maximum measurements of radioresistance were calculated with a solid water phantom film dosimetry using a Kodak X-OMATIC V film. The relative densities of the samples were read with a Densimetric Model 07-424, manufactured by Nuclear Associated Corporation. The density of film log of I/I$_o$ (with film/without film) was verified using a multidata water scanner system with a diode detector, in a manner known in the art.

For the samples prepared and tested, the linear attenuation coefficient for x-ray radiation was about 0.25 cm$^{-1}$ for an exposure of about 6 mV, and about 0.21 cm$^{-1}$ for an exposure of about 18 mV. This compares to lead linear attenuation of about 0.53 cm$^{-1}$ for 6 mV, and 0.47 cm$^{-1}$ for 18 mV. The electron particle attenuation for an approximately 8.2 millimeter thick shield on an approximately 9 MeV therapeutic beam was complete, and reduced an approximately 12 MeV beam to about 9.7%. While approximately one millimeter of elemental lead is capable of stopping a 2 MeV beam, one millimeter of the preferred bismuth-filled thermoplastic material was able to stop a 1.1 MeV beam, evidencing an efficiency of approximately half that of lead. The samples were each irradiated at about 7600 cGy, and subsequently exhibited no loss of attenuation of radioresistivity, pliability or moldability when heated to about 50° C. and refitted as radiation shield.

In view of the above, it can be seen that the metal-filled reversible-state thermoplastic shield of this invention provides distinct advantages over prior art shielding devices, including lead-filled clay shields and shields formed from thermosetting materials. For example, a significant advantage of the shield of the present invention is the use of stable materials that are nontoxic, noncarcinogenic and nonhazardous, enabling the use of the shield for both intra and extra oral impression and molding. The preferred bismuth particles and hydrocarbon wax blend are stable and compatible with each other, allowing high homogeneous loading of the bismuth to maximize the radiation shielding effect.

Another significant advantage is the ability of the shield to readily capture fine anatomic detail, and subsequently attain a rigid state after molding that reliably preserves the desired detail. In particular, the thermoplastic materials described herein are characterized by being a solid at temperatures of about 35° C. and below, yet readily moldable at about 45° C. (i.e., well within human tolerance levels) to accurately capture the anatomy to be protected. Once completely solidified, the shield can also be easily trimmed with a rotary bur or lathe if necessary.

Furthermore, the thermoplastic materials of this invention do not set irreversibly, but instead undergo a reversible change of state, such that repeated adjustments can be made in clinical situations for a more precise sized and configured shield. Should a greater thickness be required or a change occur in the shape field to be irradiated, the shield of this invention can be readily reheated and reshaped to the desired configuration in situ or by hand. Such a capability is in contrast to prior art thermosetting compounds that undergo an irreversible base-catalyst polymerization reaction, and therefore cannot be subsequently remolded. The preferred bismuth-filled thermoplastic material of this invention cools sufficiently slowly to provide an ample working time for molding and remolding the shield to achieve a proper fit.

Yet another significant advantage of this invention over prior art radiation shields, and particularly that taught by Eichmiller, is the ability of the preferred thermoplastic materials to be mixed for extended periods when mixed dry or maintained at a suitable elevated temperature. The fine granulated thermoplastic and metal particles can be thoroughly blended in a single container for extended periods of time, and then immediately heated to maintain the uniform distribution of the metal particles. As such, radiation shields in accordance with this invention can be readily produced to have a uniform radioresistivity. To ensure consistency, shield preforms can be produced in bulk for specific modalities of cancer therapy and to have a predetermined and appropriate radioresistance for such modalities, prior to clinic use and patient customization. The result is a more consistent, reliable and safer product for wide use in the radiotherapy field.

While our invention has been described in terms of a preferred embodiment, it is apparent that other forms could be adopted by one skilled in the art, for example by modifying the processing and fabrication parameters such as the molding and reheating temperatures suggested, or by substituting appropriate materials, or by utilizing the metal-filled thermoplastic shield of this invention in alternative applications. Accordingly, the scope of our invention is to be limited only by the following claims.

The embodiments of the invention in which an exclusive property or privilege is claimed are defined as follows:

1. A radiation shielding compound comprising metal particles uniformly dispersed in a thermoplastic matrix, the metal particles being formed from a nontoxic, nonradioactive and radioresistant metal or metal alloy, the thermoplastic matrix being a thermoplastic material characterized as a solid at temperatures of up to about 35° C. and being plastically formable at temperatures of about 45° C. and higher.

2. A radiation shielding compound as recited in claim 1 wherein the metal particles are formed from a metal selected from the group consisting of bismuth, silver, copper, tin, palladium, lead and alloys thereof.

3. A radiation shielding compound as recited in claim 1 wherein the thermoplastic material is a hydrocarbon wax blend.

4. A radiation shielding compound as recited in claim 3 wherein the hydrocarbon wax blend comprises about 30 parts rosin, about 30 parts copal resin, about 10 parts carnauba wax, about 4 parts stearic acid, and about 75 parts talc.

5. A radiation shielding compound as recited in claim 1 further comprising a backscatter layer, the backscatter layer comprising the thermoplastic material.

6. A radiation shielding compound as recited in claim 1 wherein the metal particles and the thermoplastic material are admixed in a ratio of about 50:50 to about 65:35, respectively.

7. A radiation shielding device formed from the radiation shielding compound recited in claim 1.

8. A radiation shielding device comprising bismuth particles uniformly dispersed in a thermoplastic matrix, the thermoplastic matrix being a hydrocarbon wax blend characterized as a solid at temperatures of up to about 35° C. and being plastically formable at temperatures of about 45° C. and higher.

9. A radiation shielding device as recited in claim 8 wherein the hydrocarbon wax blend comprises about 30 parts rosin, about 30 parts copal resin, about 10 parts carnauba wax, about 4 parts stearic acid, and about 75 parts talc.

10. A radiation shielding device as recited in claim 8 further comprising a backscatter layer, the backscatter layer comprising the hydrocarbon wax blend.

11. A radiation shielding device as recited in claim 8 wherein the bismuth particles and the hydrocarbon wax blend are admixed in a ratio of about 50:50 to about 65:35, respectively.

12. A method for forming a radiation shielding device, the method comprising the steps of:

combining metal particles and a thermoplastic powder so as to achieve a uniform dispersion of the metal particles within the thermoplastic powder, the metal particles being formed from a nontoxic, nonradioactive and radioresistant metal or metal alloy, the thermoplastic powder being a thermoplastic material characterized as a solid at temperatures of up to about 35° C. and being plastically formable at temperatures of about 45° C. and higher;

heating the metal particles and the thermoplastic powder to a temperature sufficient to melt the thermoplastic powder and thereby form a molten mixture; and cooling the molten mixture so as to form a solid in which the metal particles are dispersed in the thermoplastic material.

13. A method as recited in claim 12 wherein the metal particles are formed from a metal selected from the group consisting of bismuth, silver, copper, tin, palladium, lead and alloys thereof.

14. A method as recited in claim 12 wherein the thermoplastic material is a hydrocarbon wax blend.

15. A method as recited in claim 14 wherein the hydrocarbon wax blend comprises about 30 parts rosin, about 30 parts copal resin, about 10 parts carnauba wax, about 4 parts stearic acid, and about 75 parts talc.

16. A method as recited in claim 12 further comprising the steps of forming a backscatter layer of the thermoplastic material and adhering the backscatter layer to the radiation shielding device.

17. A method as recited in claim 12 wherein the metal particles and the thermoplastic material are admixed in a ratio of about 50:50 to about 65:35, respectively.

18. A method as recited in claim 12 further comprising the steps of reheating the solid to a temperature of at least about 45° C. such that the solid becomes plastically formable, molding the solid so as to achieve a shape for the radiation shielding device, and then cooling the radiation shielding device such that the radiation shielding device retains the shape.

19. A method as recited in claim 18 wherein the molding and cooling steps are performed while the radiation shielding device is in contact with a human subject.

20. A method as recited in claim 18 wherein the molding and cooling steps are performed intra orally on a human subject.

* * * * *